United States Patent [19]

Johansson

[11] Patent Number: 4,615,220
[45] Date of Patent: Oct. 7, 1986

[54] METHOD AND DEVICE FOR MEASURING SMALL FORCES AND SMALL MOVEMENTS IN A MATERIALS TESTING MACHINE OR OTHER LOADING DEVICE

[75] Inventor: Anders I. Johansson, Farsta, Sweden

[73] Assignee: AB Sandvik Hard Materials, Stockholm, Sweden

[21] Appl. No.: 749,396

[22] Filed: Jun. 27, 1985

[30] Foreign Application Priority Data

Jul. 12, 1984 [SE] Sweden ............................. 8403684

[51] Int. Cl.[4] ............................................. G01N 3/00
[52] U.S. Cl. ................................... 73/789; 73/862.65
[58] Field of Search ................. 73/818, 819, 820, 821, 73/822, 824, 825, 849, 851, 862.62, 862.63, 862.64, 862.65, 862.66, 862.67, 862.04, 862.53, 862.54, 862.52, 789

[56] References Cited

U.S. PATENT DOCUMENTS

| | | | |
|---|---|---|---|
| 2,421,222 | 5/1947 | Schaevitz | 73/862.52 |
| 2,612,774 | 10/1952 | Zener et al. | 73/789 X |
| 2,677,190 | 5/1954 | Shaw et al. | 33/DIG. 13 X |
| 2,826,062 | 3/1958 | Brown et al. | 73/789 X |
| 3,495,448 | 2/1970 | Young, Jr. | 73/834 |
| 3,911,737 | 10/1975 | Ormond | 73/862.65 |
| 4,491,027 | 1/1985 | Yalof et al. | 73/862.52 |

Primary Examiner—Jerry W. Myracle
Attorney, Agent, or Firm—Burns, Doane, Swecker & Mathis

[57] ABSTRACT

The invention relates to a method of attaining a rigid loading device for simultaneous measuring of small forces and small movements in a testing machine intended for greater forces and movements. According to the invention a preferably annular yoke (20) dimensioned to carry the loading capacity of the testing machine, is applied in the testing machine. By using the well-defined relationship between force and deformation of the yoke, the deformation of a test piece (11) placed within the yoke is measured and controlled. At the same time the force against the test piece is measured by a force transducer (10) also placed within the yoke. The measuring range of said force transducer is chosen to meet the required load capacity for the testing.

20 Claims, 4 Drawing Figures

METHOD AND DEVICE FOR MEASURING SMALL FORCES AND SMALL MOVEMENTS IN A MATERIALS TESTING MACHINE OR OTHER LOADING DEVICE

BACKGROUND OF THE INVENTION

The present invention relates to a method and a device for accurate control and measurement of small forces and small movements in a loading device intended for essentially greater forces and movements.

Investigation of the mechanical properties of metals or other materials demands careful measurements of the load and of the deformation of a test piece caused by said load, i.e. a simultaneous measurement of load and movement.

Materials testing laboratories have normally access to testing machines with a load capacity from 50 kN and upwards. In tests demanding considerably smaller loads, about 1000N or less, the prescribed accuracy in determining the load can often not be attained.

A frequently used method of solving said problem is to insert an additional force transducer with suitable measuring range in series with the test piece. At tension loads this solution can be possible because the transducer can be protected against harmful overloads occurring for instance when the test piece breaks. On the other hand, at compressive loads it is difficult to protect the force transducer effectively against such harmful overloads. This depends upon the fact that it is difficult to operate the (often servo controlled) machine with sufficient accuracy. It may also result in that the test piece is exposed to harmful overloads and may break already when it is affixed in the machine.

For test pieces having very low strength, devices for measuring the deformation (extensometers) can give rise to forces against the test pieces which influence the fracture behaviour and the measured forces in a non-acceptable way.

The purpose of the present invention is to provide a method which eliminates the above mentioned disadvantages when for example a testing machine is used for determination of the bending, compressive or tensile strengths or of the fracture toughness, within a loading range for which the machine is not intended to be used.

The principle is based upon the physical fact that, in a suitably designed annular body, yoke, loaded in two diametrically opposite points, a well-defined usually linear relationship between force and deformation, D, is obtained within the elastic range, D being measured as the displacement of said points in relation to each other in the direction of the force.

Closer details of an embodiment of the invention will be evident from the following specification with drawings belonging to it, showing:

DETAILED DESCRIPTION OF THE PREFERRED EMBODIMENTS

Figure 1:
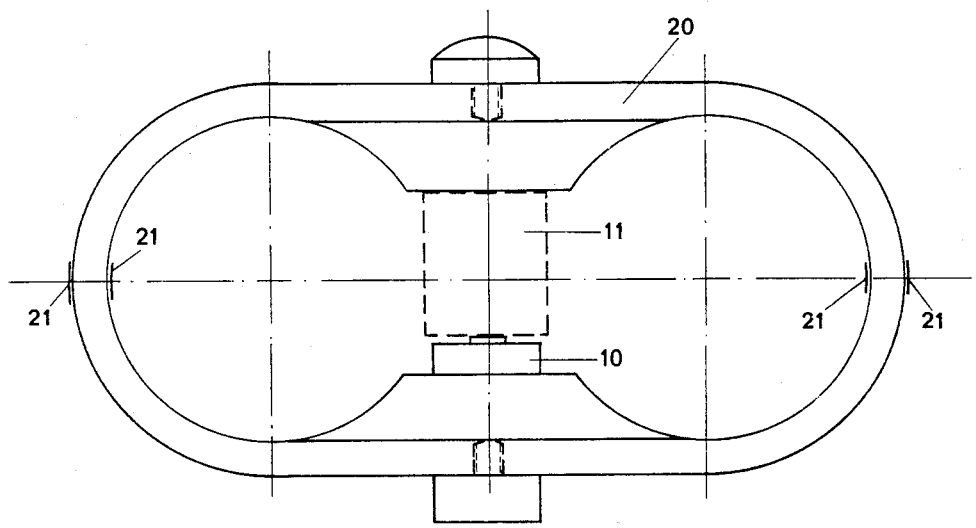
FIG. 1. is a side view of a measuring yoke according to the invention.
Figure 2:
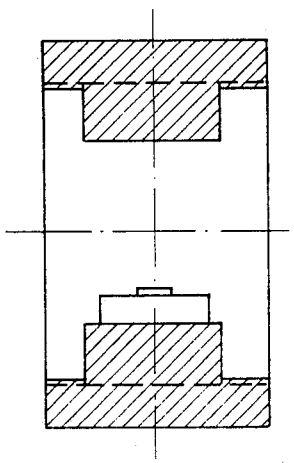
FIG. 2. is a cross-sectional view of the measuring yoke in FIG. 1.

The invention includes using a preferably annular yoke 20 according to FIG. 1. Within the yoke an inner force transducer 10 and a testing fixture 11 acting against said transducer are placed. The measuring range of the force transducer is selected so that it exceeds the expected maximum force during the test with a suitable margin. The yoke shall be dimensioned so that required movement is obtained without the elastic limit of the yoke material being exceeded and preferably so that it can carry the maximum load of the machine without being damaged.

Figure 3:
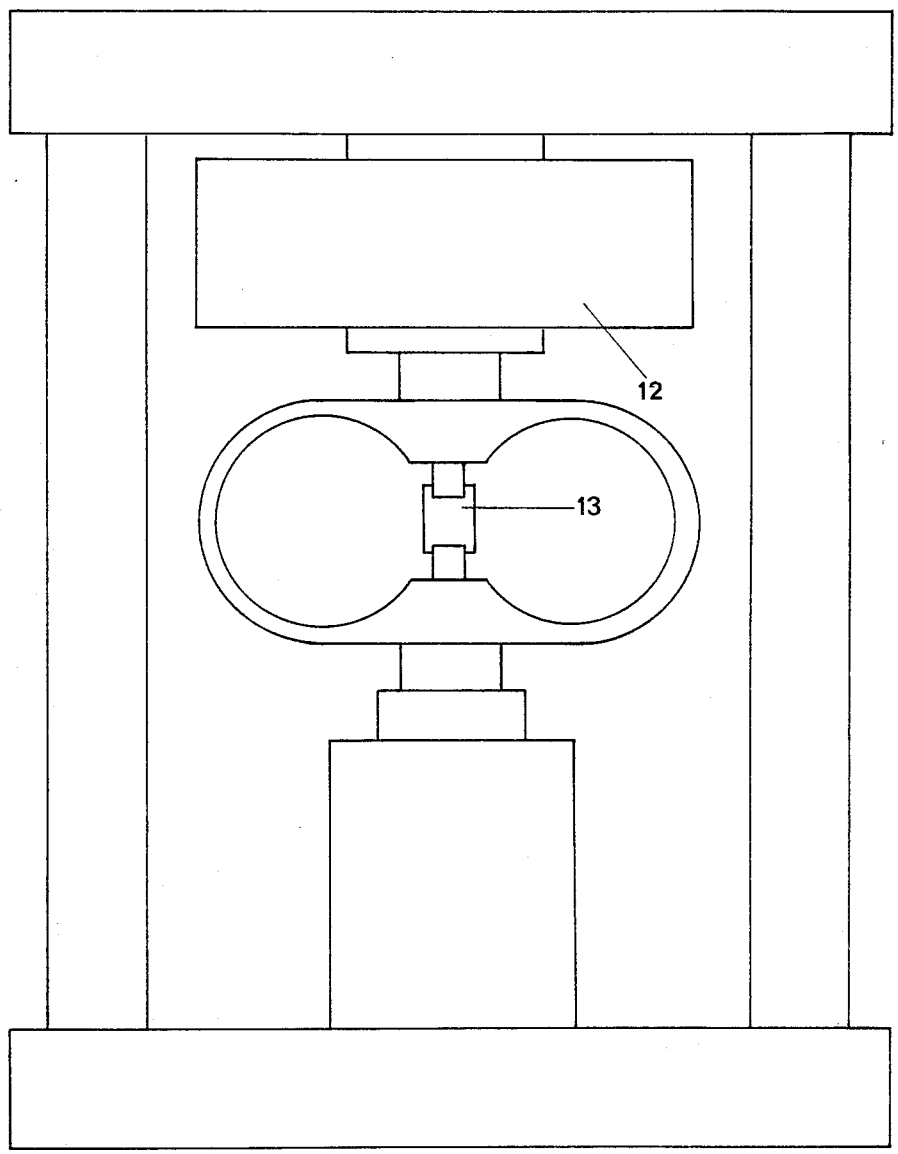
FIG. 3. is a side view of the measuring yoke mounted in a testing machine for calibration.

Before the test the measuring yoke shall be calibrated. The deformation a function of the applied force is measured by means of an outer force transducer 12 in FIG. 3 and an accurate extensometer 13 in FIG. 3. A linear relationship between force and deformation is obtained in accordance with the expression.

$$D = k_1 F_b$$

wherein
  wherein D = Deformation is $\mu$m, measured by the extensometer,
  $F_b$ = Force against the measuring yoke measured by the outer force transducer, and
  $k_1$ = Proportionality constant.

Materials testing machines are normally operated in load control mode and the loading rate can be varied within wide limits by a ramp function. Because of the aforementioned linear relationship between force increase and deformation, the displacement of the loading points relative to each other will be proportional to and follow the same time course as the force against the measuring yoke. This relationship is valid when the inner force transducer is unloaded and approximately also when the force against the same is small compared to the force against the measuring yoke. If the force against the inner transducer is not negligible, the deformation of the test piece can be obtained from the expression.

$$D = k_1(F_b' - F_p)$$

wherein
  $F_b'$ = Increase of the force against the measuring yoke during the test course, measured by the outer force transducer, and
  $F_p$ = Force against the sample, measured by the inner force transducer.

The testing fixture 11 can normally be made so rigid that its deformation can be ignored.

When testing, the measuring yoke is first loaded with such a force that a suitable pre-load on the test piece is obtained. During the following ensuing load increase the force course and the rupture force are indicated by the inner force transducer. The deformation course and the rupture deformation are indirectly indicated by the outer force transducer. The fracture strength value is then calculated in a conventional way on the basis of the dimensions of the test piece and the indicated fracture load. Energy absorbed before rupture is calculated as the integral of the product of force and deformation up to fracture. The modulus of elasticity is obtained from the relationship between force, deformation and the dimensions of the test piece.

Alternatively, the deformation of the yoke during the testing course—and thus also the deformation of the test piece—can be determined by separate means, for example strain gauges 21 placed at suitable points of the yoke 20.

This alternative can also be used if a particularly rigid testing device is needed. The inner force transducer 10 can then be excluded and the force against the test piece, $F_p$, may instead be determined from the following relationship:

$$D=(F_b-F_p)k_2$$

wherein

D = Deformation, measured by separate means, and
$k_2$ = Proportionality constant, determined by calibration.

EXAMPLE

For accurate determination of the strength properties of powder compacts in three point bending test there was available a computer operated servo controlled testing machine with a maximum load capacity of 100 kN and with the load ranges 100-50-20-10 kN. For powder compacts with the dimensions 8×6×25 mm the fracture force amounts to at the most 100N and the deflection at fracture is 100–300 μm.

Figure 4:
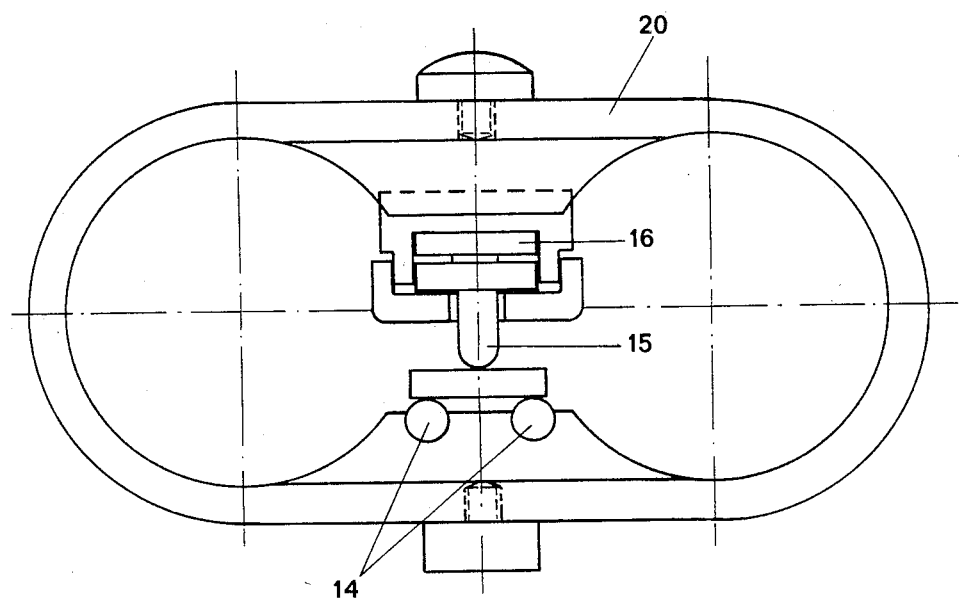
FIG. 4. is a side view of the measuring yoke being used during a test procedure.

A measuring yoke according to the invention with grooves for the two support rolls 14 for three point bending test (see FIG. 4) was made of SS 2541 material. For applying the load on the test piece a punch 15 of the same material was used. A miniature compression force transducer 16, Showa MR 10 K, was used for determination of the force against the test piece.

Before the test the yoke was calibrated and its deformation, D in μm as function of the applied force, F in N, was determined by means of the force transducer of the testing machine and an extensometer, MTS Model 632.05C-62 with measuring range ±0.5 mm. The following relationship was obtained:

$$D=0.0734F_b$$

The displacement of the punch 15 will be proportional to and follow the same time course as the resulting force against the measuring yoke ($F_r$). The displacement of the punch is obtained from $$D=0.0734F_r$$

where $F_r=F_b'-F_p$

The relationship D as function of $F_b$ is calculated "on-line" by the computer connected to the testing machine.

The load-deflection curve of each separate test piece was displayed on the graphical screen of the computer. The following quantities were calculated by the computer and presented on the screen: fracture load, deflection at fracture, transverse rupture strength, Young's modulus and energy absorbed before rupture. After each test series, which normally included six test pieces, also the corresponding mean values were calculated.

In a series of six hard metal powder compacts pressed to a relative density of 56%, the following mean values were obtained:

Fracture load: 27.3N
Deflection at fracture: 254 μm
Transverse rupture strength: 1.95N/mm$^2$
Energy absorbed before rupture: 2.57 mJ
Modulus of elasticity: 52N/mm$^2$ The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing detailed description should be considered exemplary in nature and not limited to the scope and spirit of the invention as set forth in the appended claims.

What is claimed is:

1. Apparatus for measuring small forces and small movements in a testing machine intended for considerably greater forces and movements, comprising a yoke dimensioned to carry the loading capacity of the testing machine and mountable within the testing machine, said yoke including a test fixture positioned within the yoke for transmitting a load from the yoke at its deformation to a test piece positioned within the test fixture and a force transducer placed in the force path within the yoke for measuring said force applied to the test piece.

2. Apparatus according to claim 1, wherein said yoke is substantially annular.

3. Method of obtaining a rigid loading device for simultaneously measuring small forces and small movements in a testing machine intended for greater forces and movements, the testing machine having a first force transducer, comprising the steps of:

positioning in said testing machine a yoke for application of a force to a test fixture, said yoke being dimensioned to carry the maximum load of the testing machine;

applying a test force to the yoke;

measuring the force applied to the yoke by using the first force transducer to establish a relationship between force and deformation of the yoke, said deformation being measured using an extensometer;

affixing the test fixture within the yoke, the test fixture having a second force transducer, said second force transducer having a measuring range substantially similar to the required load for the test;

positioning a test piece within the test fixture;

applying a force to the yoke; and measuring with said second force transducer the force against the test piece while simultaneously measuring the force on the yoke with the first force transducer to determine the deformation of the test piece.

4. Method according to claim 3, wherein the relationship between force and deformation of the yoke is linear.

5. Method according to claim 4, wherein the load on the yoke is measured by the force transducer of the testing machine.

6. Method according to claim 3, wherein said yoke is substantially annular.

7. The method according to claim 3, further comprising the step of controlling the force applied by the testing machine to the test piece by monitoring the force applied to the yoke.

8. The method of claim 18, wherein the force applied to the yoke is controlled such that the force applied to the test piece is linear.

9. Method of obtaining a rigid loading device for simultaneously measuring small forces and small movements in a testing machine intended for greater forces and movements, the testing machine having a first force transducer, comprising the steps of:

positioning in said testing machine a yoke for application of a force to a test fixture, said yoke having a predetermined relationship between force and deformation, said yoke being dimensioned to carry the maximum load of the testing machine;

affixing the test fixture within the yoke, the test fixture having a second force transducer, said second force transducer having a measured range substantially similar to the required load for the test;

positioning a test piece within the test fixture;

applying a force to the yoke; and measuring with said second force transducer the force against the test piece while simultaneously measuring the force on the yoke with the first force transducer to determine the deformation of the test piece.

10. The method according to claim 9, further comprising the step of controlling the force applied by the testing machine to the test piece by monitoring the force applied to the yoke.

11. The method of claim 10, wherein the force applied to the yoke is controlled such that the force applied to the test piece is linear.

12. Method according to claim 9, wherein the relationship between force and deformation of the yoke is linear.

13. Method of obtaining a rigid loading device for simultaneously measuring small forces and small movements in a testing machine intended for greater forces and movements, said testing maching having a first force transducer, comprising the steps of:

positioning in said test machine a yoke for application of a force to a test fixture;

measuring the deformation of said yoke with separate measuring means positioned at predetermined locations on the yoke to establish a relationship between the deformation of the yoke and the applied force, said yoke being dimensioned to carry the maximum load of the testing machine;

affixing the test fixture within the yoke;

positioning a test piece within the test fixture;

applying a force to the yoke; and measuring the deformation of the yoke by said separate measuring means while measuring the force on the yoke to determine the load on the test piece from the actual deformation and load and the relationship between the deformation and the force of the yoke.

14. Method according to claim 13, wherein said separate measuring means includes a strain gauge.

15. The method according to claim 13, further comprising the step of controlling the force applied by the testing machine to the test piece by monitoring the force applied to the yoke.

16. The method of claim 15, wherein the force applied to the yoke is controlled such that the force applied to the test piece is linear.

17. Method of obtaining a rigid loading device for simultaneously measuring small forces and small movements in a testing machine intended for greater forces and movements, said testing machine having a first transducer, comprising the steps of:

positioning in said test machine a yoke for application of a force to a test fixture, said yoke having separate measuring means positioned at predetermined positions on the yoke, said yoke having a predetermined relationship between deformation and force, said yoke being dimensioned to carry the maximum load of the testing machine;

affixing the test fixture within the yoke;

positioning a test piece within the test fixture;

applying a force to the yoke; and measuring the deformation of the yoke by said separate measuring means while measuring the force on the yoke to determine the load on the test piece from the actual deformation and load and the relationship between the deformation and the force of the yoke.

18. Method according to claim 17, wherein said separate measuring means includes a strain gauge.

19. The method according to claim 17, further comprising the step of controlling the force applied by the testing machine to the test piece by monitoring the force applied to the yoke.

20. The method of claim 19, wherein the force applied to the yoke is controlled such that the force applied to the test piece is linear.

* * * * *